(12) United States Patent  (10) Patent No.: US 6,352,549 B1
Everett  (45) Date of Patent: Mar. 5, 2002

(54) MEDICAL DEVICE FOR APPLYING HIGH ENERGY LIGHT AND HEAT FOR GYNECOLOGICAL STERILIZATION PROCEDURES

(75) Inventor: Royice B. Everett, Edmond, OK (US)

(73) Assignee: MyriadLase, Inc., Oklahoma City, OK (US)

( * ) Notice: Subject to any disclaimer, the term of this patent is extended or adjusted under 35 U.S.C. 154(b) by 1358 days.

(21) Appl. No.: 08/592,006

(22) Filed: Jan. 26, 1996

Related U.S. Application Data

(63) Continuation of application No. 08/155,091, filed on Nov. 19, 1993, now abandoned, which is a continuation of application No. 07/895,940, filed on Jun. 9, 1992, now abandoned, which is a continuation of application No. 07/498,349, filed on Mar. 23, 1990, now Pat. No. 5,147,353.

(51) Int. Cl.[7] .............................................. A61B 17/36

(52) U.S. Cl. .............................. 607/92; 606/15; 606/28; 606/135

(58) Field of Search ................................ 606/15, 28, 2, 606/4, 27, 135, 193, 29, 12, 113; 128/831; 607/92; 372/35

(56) References Cited

U.S. PATENT DOCUMENTS 3,858,586 A * 1/1975 Lessen ........................ 128/831
5,107,513 A * 4/1992 Sagie et al. .................... 372/35

* cited by examiner

Primary Examiner—Mark S. Graham
(74) Attorney, Agent, or Firm—McAfee & Taft

(57) ABSTRACT

A localized heat applying medical device is provided for applying heat to tissue adjacent a patient's tubal ostia in order to close the patient's fallopian tubes and sterilize the patient. Procedures of performing sterilizations are also disclosed.

16 Claims, 3 Drawing Sheets

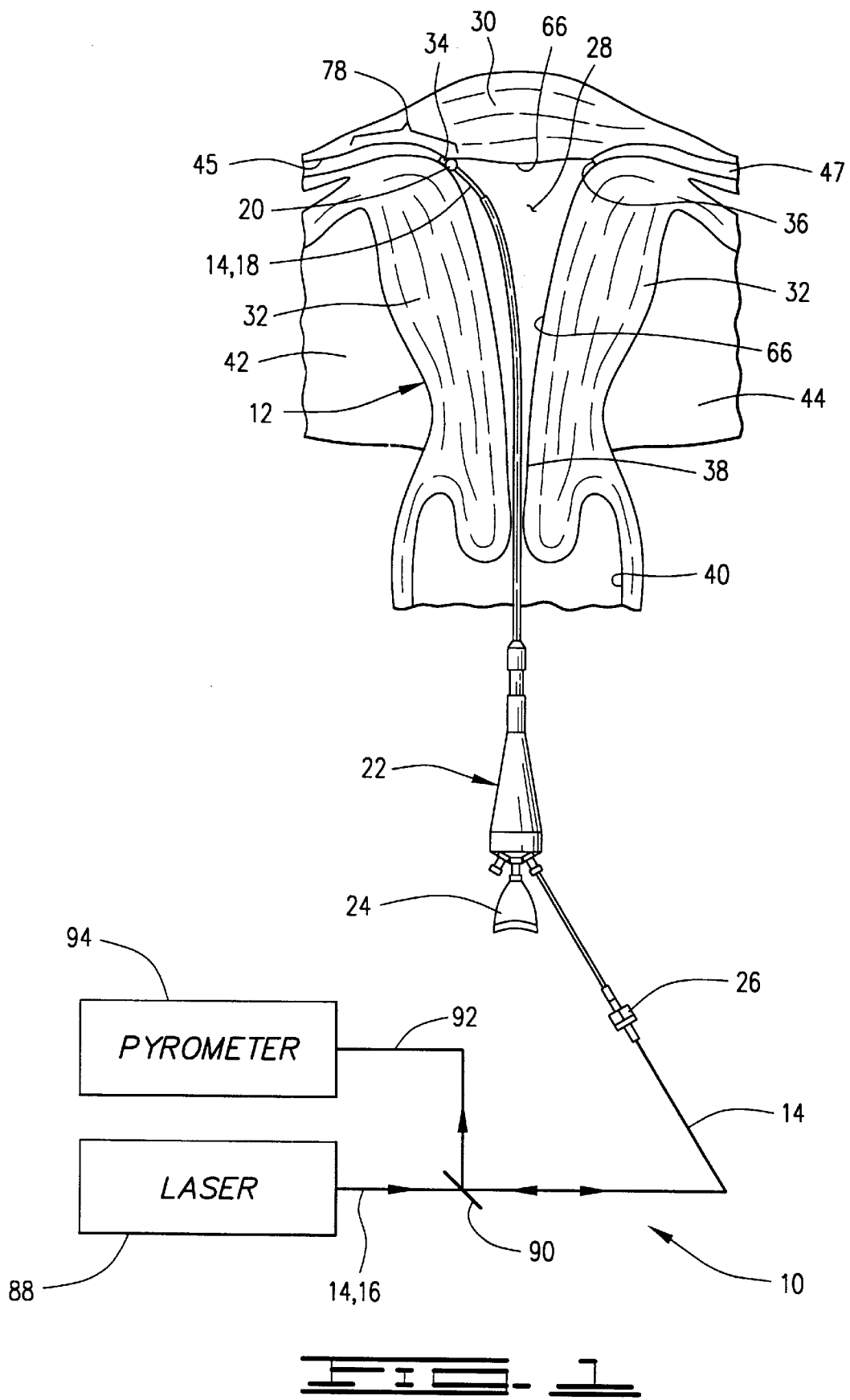

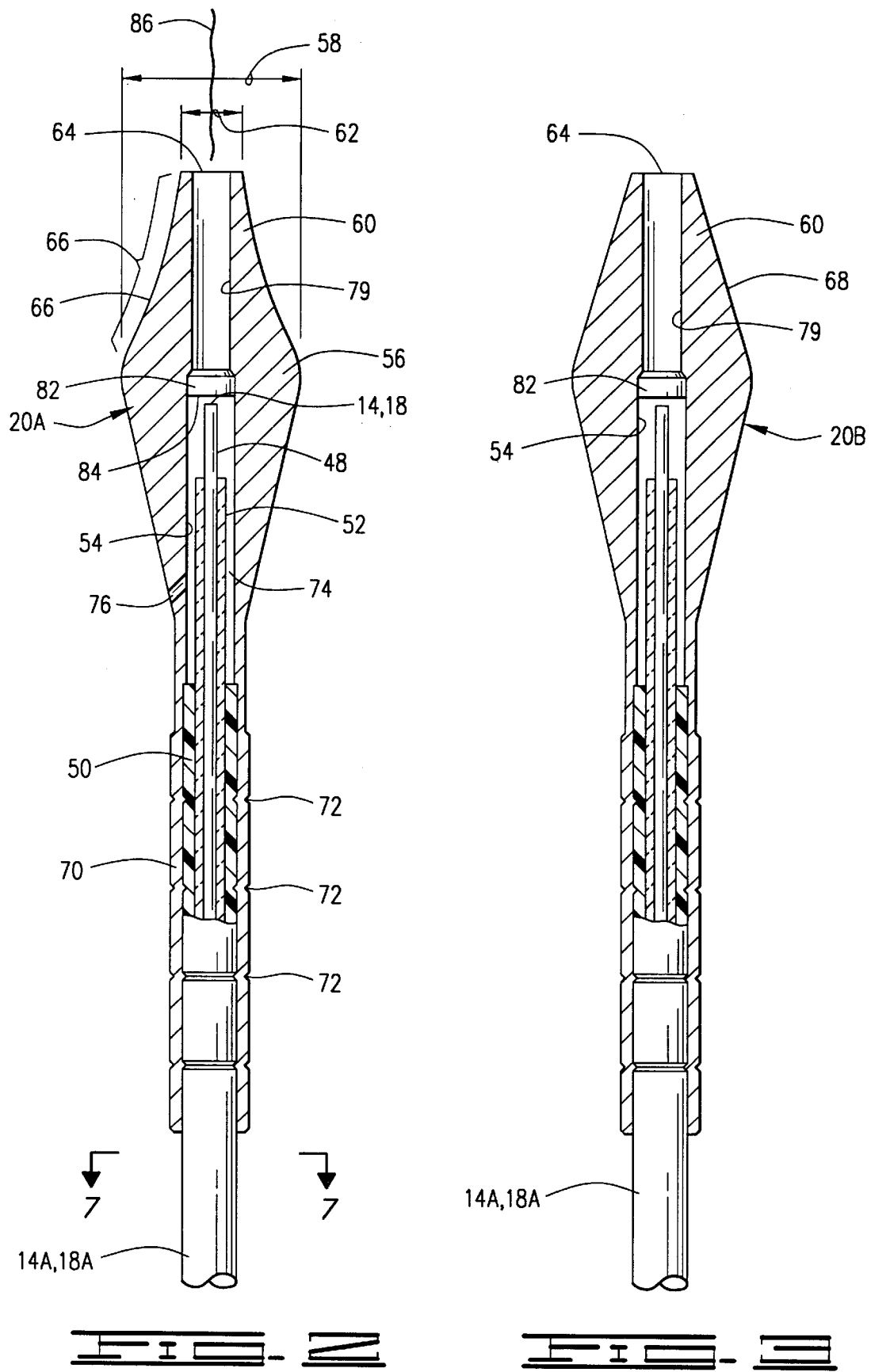

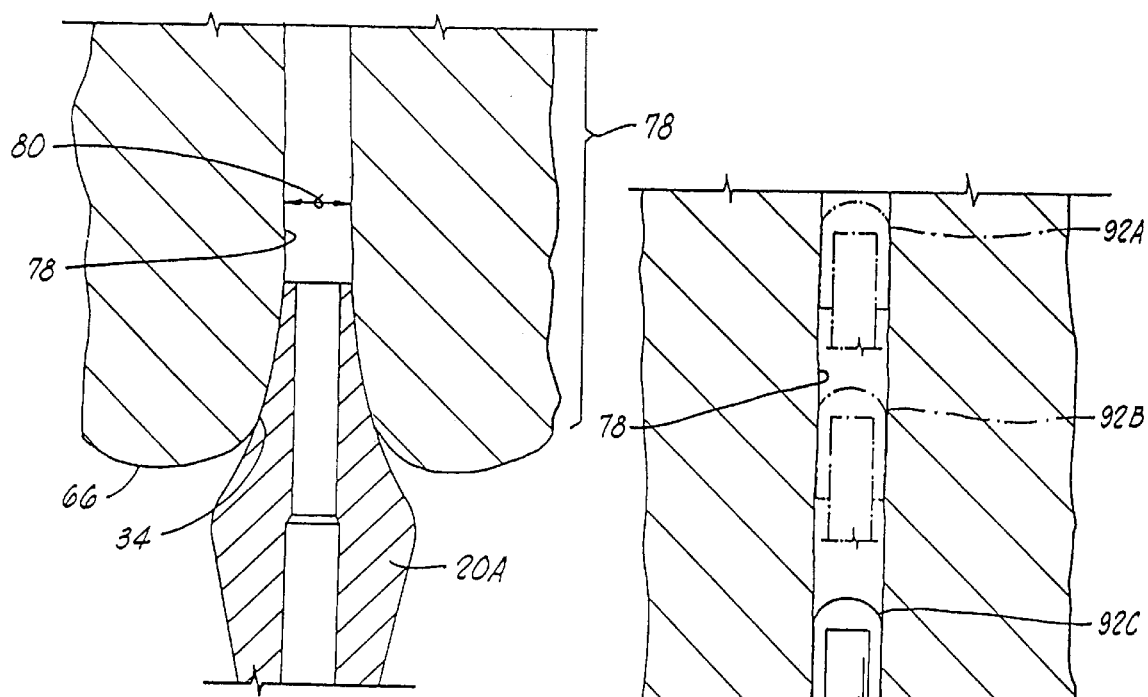
FIG. 4
FIG. 6
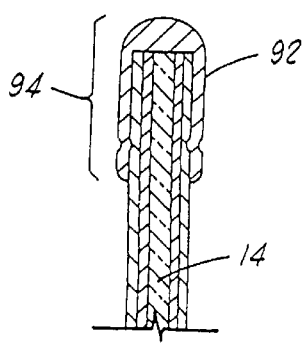
FIG. 5
PRIOR ART
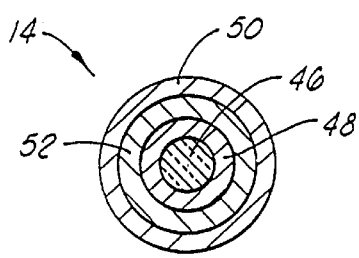
FIG. 7

MEDICAL DEVICE FOR APPLYING HIGH ENERGY LIGHT AND HEAT FOR GYNECOLOGICAL STERILIZATION PROCEDURES

This is a continuation of applications Ser. No. 08/155,091 filed on Nov. 19, 1993, abandoned which is a continuation of application Ser. No. 07/895,940 filed Jun. 9, 1992, which is a continuation of application Ser. No. 07/498,349 filed Mar. 23, 1990, now U.S. Pat. No. 5,147,353.

BACKGROUND OF THE INVENTION

1. Field of the Invention

The present invention relates to medical devices and procedures for applying localized heat to a site in the patient's body, particularly for purposes such as sterilization of a female patient by closing of the fallopian tubes.

2. Description of the Prior Art

The prior art includes devices and procedures for applying localized heat to a site in a patient's body for a number of purposes, generally including altering, removing or destroying tissue in a patient's body.

U.S. Pat. Nos. 4,773,413 and 4,662,368 both to Hussein et al. disclose a localized heat applying medical device powered by laser energy transmitted through an elongated conduit. The heat applying device includes a bulbous heat generating element, having an aperture in the forward end of the device permitting a portion of the laser energy to be transmitted out the aperture and directly applied to the patient's body tissue. The devices disclosed in Hussein et al. are particularly designed for use in treating cardiovascular disease by removing arteriosclerotic deposits from blood vessels. Commercial embodiments of the Hussein et al. device are marketed by LaserControl Medical Systems Division of Trimedyne, Inc., of Santa Ana, Calif. One such commercially available device is marketed as the Spectraprobe™-80, which is designed such that approximately eighty percent of the laser energy transmitted thereto is emitted through the optical aperture at the end of the device. The Spectraprobe™-80 has a tip diameter of about 2.5 millimeters.

German Patent No. 2,826,383, published Dec. 20, 1979, of Eichler et al., discloses a laser probe placed directly against or inserted into the patient's tissue for treating the same.

It is also known to use laser powered devices in hysteroscopic procedures. For example, a surgical procedure referred to as an "endometrial ablation" has been recently developed as an, alternative to hysterectomy for treatment of excessive uterine bleeding. In this procedure, an Nd:YAG laser is used to destroy the entire endometrium lining the uterus. An optical fiber is inserted in the uterus by means of a hysteroscope to conduct the laser energy to the endometrium. With the aid of a parallel optical viewing fiber of the hysteroscope, the end of the laser transmitting fiber is slowly moved across the surface of the endometrium so that the laser energy penetrates and destroys the endometrium which is on the order of three millimeters thick. Typical prior art procedures have utilized a bare optical fiber for transmitting the laser energy. Two techniques have been developed. By one technique, the end of the bare optic fiber is actually touched to the endometrium in a "dragging" procedure. By a second technique, generally referred to as "blanching", the bare tip of the optic fiber is held several millimeters away from the endometrium. These techniques are generally described in Daniell et al., "Photodynamic Ablation Of The Endometrium With The ND:YAG Laser Hysteroscopically As A Treatment Of Menorrhagia", *Colposcopy and Gynecologic Laser Surgery*, Volume 2, No. 1, 1986; Mackety, "Alternative To Hysterectomy: Endometrial Ablation By Laser Photovaporization", *Today's OR Nurse*, Volume 8, No. 4; and Goldrath et al., "Laser Photovaporization Of Endometrium For The Treatment Of Menorrhagia", *AM. J. Obstet. Gynecol.*, Volume 140, No. 1, page 14, May 1, 1981.

The Goldrath et al. and Daniell et al. articles cited above, both suggest that patients undergoing an endometrial ablation procedure will probably be sterile following the procedure. The work of Goldrath et al. and Daniell et al. was not directed to the end purpose of sterilization, but it was observed as a side effect of the treatment. For reasons further described herein, it is believed that the cause of the sterility observed by Goldrath et al. and Daniell et al. was the destruction of the patient's endometrium.

A recent improvement upon the endometrial albation procedure, wherein a heat generating tip is attached to the end of the laser transmitting conduit, with the tip being designed to laterally emit a portion of the laser energy is disclosed in Everett et al. pending Application No. PCT/US89/02492 filed Jun. 7, 1989, which has been published as International Publication No. WO 89/11834 on Dec. 14, 1989. That application is a continuation-in-part of U.S. patent application Ser. No. 205,218 filed Jun. 10, 1988.

In all of the endometrial ablation procedures set forth in the references discussed above, the treatment is directed to the endometrium, that is the lining of the uterine cavity, for the purpose of destroying that lining to prevent excessive bleeding. The procedures are not directed to the purpose of closing the fallopian tubes to induce sterilization. Furthermore, the endometrial ablation procedures do not involve any substantial fixed contact of the tip of the laser fiber, or of a heating device on the end of the laser fiber, with the tissue, but rather involve a continuous movement of the tip while dragging it across, or moving it while held a slight distance away from, the tissue.

SUMMARY OF THE INVENTION

The present invention provides procedures for sterilizing patients by the use of heat and laser light energy applied by holding a heating device in fixed contact with tissue adjacent the tubal ostia in order to coagulate the interstitial portion of the fallopian tubes thereby closing the fallopian tubes. Localized heat applying devices are provided which are particularly adapted for use in such procedures.

A localized heat applying medical device for applying heat to tissue adjacent a patient's tubal ostia in order to close the patient's fallopian tubes and sterilize the patient includes an elongated light transmitting conduit having a proximal end and a distal end. A bulbous heat generating means is mounted on the distal end of the conduit for converting light energy transmitted by the conduit in part to heat thereby raising the temperature thereof. The bulbous heat generating means has a larger portion with an outside diameter of at least about two millimeters, and has a tapered forward portion with a forwardmost tip having an outside diameter no greater than about one millimeter, so that the tip can be received through one of the tubal ostia with the larger portion of the bulbous heat generating means engaging an inner wall of the patient's uterus adjacent said one of the tubal is ostia. The bulbous heat generating means includes a light transmitting aperture means extending through the tapered-forward portion to the tip for enabling light energy transmitted by the conduit in part to pass through the aperture means into the fallopian tube associated with said one of the tubal ostia.

Procedures utilizing such a device include steps of inserting into the patient's uterus the elongated laser light energy transmitting conduit having the heat generating device on the distal end thereof. Then the heat generating device is maintained in fixed contact with the inner wall of the patient's uterus adjacent the tubal ostia for a sufficient time and while transmitting sufficient energy to the heat generating device to coagulate a substantial part of the interstitial portion of the patient's fallopian tubes to close the same.

Numerous objects, features and advantages of the present invention will be readily apparent to those skilled in the art upon a reading of the following disclosure when taken in conjunction with the accompanying drawings.

BRIEF DESCRIPTION OF THE DRAWINGS

FIG. 1 is a schematic illustration including a cross-sectional view of the anatomy of the patient's uterus, with a localized heat applying device held in place therein by means of a hysteroscope with which is associated a laser energy source.

FIG. 2 is a cross-sectional illustration of a first preferred embodiment of the heat generating device connected to the distal end of the laser transmitting conduit. The heat generating device has a tapered forward end with a concave profile.

FIG. 3 is a view similar to FIG. 2 of a second preferred embodiment of the heat generating device, having a frusto-conical tapered forward end.

FIG. 4 is a schematic illustration of the device of FIG. 2 with its tapered forward end portion inserted into one of the patient's tubal ostia so as to center the heat generating device about the tubal ostia and against the inner wall of the patients uterus.

FIG. 5 is a cross-sectional view of a generally cylindrical heat generating means, which itself is a part of the prior art.

FIG. 6 is a schematic illustration of a procedure utilizing a cylindrical heat generating means like that of FIG. 5 in a procedure wherein it is completely inserted into the interstitial portion of the fallopian tube and then sequentially heated at several locations.

FIG. 7 is a cross-sectional view taken along line 7—7 of FIG. 2.

DETAILED DESCRIPTION OF THE PREFERRED EMBODIMENTS

The present invention is a medical device for applying localized heat to tissue adjacent a patient's tubal ostia in order to close the patient's fallopian tubes in the area of the interstitial portion of the fallopian tubes and to thereby sterilize the patient.

Referring to FIG. 1, a medical device 10 embodying the present invention is shown positioned within the uterus 12 of a human female patient. Device 10 includes an elongated light transmitting conduit 14 having a proximal end 16 and a distal end 18. In the particular embodiment disclosed, conduit 14 is an optical fiber for transmitting laser light energy.

The device 10 further includes a bulbous heat generating means 20 mounted on the distal end 18 of conduit 14 for converting light energy transmitted by the conduit 14 at least in part to heat thereby raising the temperature of the bulbous heat generating means 20.

The device 10 includes a conventional hysteroscope 22 which carries the light transmitting conduit 14, a parallel optical viewing fiber (not shown), and parallel fluid flow conduits (not shown). The hysteroscope 22 permits a physician to view the placement of the heat generating means 20 through the parallel optical viewing fiber. This can be observed through the eyepiece 24 of the hysteroscope 22. The hysteroscope 22 includes a connector 26 for linking with the light transmitting conduit 14. The hysteroscope is inserted in a fluid medium such as saline solution which has been placed within the uterine cavity 28.

In FIG. 1, the device 10 is shown positioned within the patient's uterine cavity 28 which is defined by an upper fundus 30 and a somewhat cylindrical side wall 32. The side wall 32 can generally be defined as extending downward from the tubal ostia 34 and 36 to the internal cervical os 38. Tubal ostia 34 and 36 communicate the uterine cavity 28 with the patient's fallopian tubes 45 and 47. The device 10 is inserted as part of the hysteroscope 22 into the uterus 12 via vaginal canal 40 and through the internal cervical os 38 using appropriate dilation procedures. The body or side wall 32 of the uterus 12 is supported by broad ligaments 42 and 44.

A first preferred embodiment of the bulbous heat generating means 20A is shown in FIG. 2 connected to the distal end 18 of light transmitting conduit 14. A second preferred embodiment of the invention is similarly shown in FIG. 3 and is designated by the numeral 20B.

The heat generating means 20A and 20B are modified forms of the heat generating means shown and described in U.S. Pat. No. 4,773,413 of Hussein et al., and particularly, the bulbous heat generating means 20A and 20B are modified forms of the device shown in FIG. 10 of U.S. Pat. No. 4,773,413. The details of construction of such heat generating means as generally described in U.S. Pat. No. 4,773,413 are incorporated herein by reference. The heat generating means 20A and 20B have been modified as compared to those of the prior art by changing their external geometry to make them more appropriate for use in the procedures disclosed herein.

The light transmitting conduit 14 is preferably a single, flexible light transmitting fiber such as used in fiber optic devices and generally has a total exterior diameter of about 600 microns or less. A single fiber generally has the rigidity needed to press the heat generating element 20 into tissue. Generally, the single light transmitting fiber or conduit 14, which is best seen in the cross-sectional view of FIG. 7, includes a core 46 surrounded by cladding 48. The internal reflection caused by the cladding 48 is such that the optical fiber 14, has a low divergence as light exits the distal end 18 thereof. The core 46 is typically made of glass, e.g., silica quartz. The cladding 48 is typically made of silicone, plastic or silica. The core 46 and its cladding 48 have a combined diameter of less than about 0.5 millimeter to about 1.0 millimeter.

To protect the core 46 and its cladding 48, the optical fiber 14 normally also includes an external jacket 50 which surrounds the cladding 48 and is held in place by a resin coating 52. The external jacket 50 is usually made of a flexible plastic material such as poly(ethylene) or poly (tetrafluoroethylene). It provides a flexible and smooth surface allowing easy manipulation of the medical device 10. Fiber optic bundles are not preferred since the adhesive between individual-fibers limits the amount of light which can be transmitted without melting of the bundle.

The optical fiber or light transmitting conduit 14 should be flexible yet sufficiently resilient so that it is possible to push the same into tissue or into the tubal ostia. One such suitable optical fiber having a core diameter of 0.4 millimeters is marketed under the designation MED 400 by Quartz Products Corporation of Plainfield, N.J. Another suitable optical fiber is a 0.6 millimeter fiber commercially available under the designation HCT 600 from Ensign Bickford Co., Conn. The power that can be transmitted along the fiber 14 varies with the size of the fiber. Utilizing the HCT 600 optical fiber, a medical device embodying this invention can transmit as much as about 60 watts continuous power from an Nd:YAG laser source.

As seen in FIG. 2, the resin coating 52 and the jacket 50 have been trimmed back from the distal end 18 of the fiber 14 leaving a section of the cladding 48 surrounding fiber core 46 pen to the sides. The distal end 18 of fiber 14 is shown received in place within a cavity 54 defined within the bulbous heat generating means 20A.

The bulbous heat generating means 20A has a larger mid portion 56 with an outside diameter 58 of at least about two millimeters. Bulbous heat generating means 20A includes a tapered forward portion 60 having an outside diameter 62 no greater than about one millimeter. As further explained below, this design permits a forward tip 64 of the tapered portion 60 to be received through one of the patient's tubal ostia with the larger portion 56 of the bulbous heat generating means 20A engaging an inner wall 66 of the uterine cavity 28 adjacent the tubal ostia 34 or 36 as best seen in FIG. 4.

As shown in FIG. 2, a longitudinal profile 66 of the bulbous heat generating means 20A is concave. This is contrasted to the heat generating means 20B of FIG. 3 which has its tapered forward portion 60 generally frusto-conical in shape with a straight profile 68.

The bulbous heat generating element 20A has a skirt portion 70 extending rearward therefrom within which is received the distal end 18 of the light transmitting conduit 14. The skirt 70 is crimped at several locations such as those designated as 72 to attach the heat generating device 20A to the jacket 50 of light transmitting conduit 14. In addition, adhesive may be used between the skirt 72 and the conduit 14.

An air space 74 is defined between the cavity 54 and the cladding 48 and resin coating 52 in the trimmed back portion of the distal end 18 of light transmitting conduit 14. A vent 76 extends through the bulbous device 20A and communicates with the air space 74 to allow an escape aperture for gases that may develop within the cavity 54.

The bulbous heat generating means 20A includes a light transmitting aperture means 79 extending forward from cavity 54 through the tapered forward portion 60 to the tip 64, for enabling light energy transmitted by the conduit 14 in part to pass through-the aperture means 79 into the interstitial portion of the fallopian tube associated therewith. Referring for example to FIG. 1, and to the enlarged view of FIG. 4, the junction between the fallopian tube 45 and the uterus 12 at the tubal ostia 34 includes an area extending generally through the wall of the uterus which is designated by the numeral 78 and which is generally referred to as the interstitial portion of the fallopian tube 45. The interstitial portion 78 is typically on the order of one centimeter in thickness. The tubal ostia 34 itself typically has a diameter 80 of from about 1.0 to about 2.0 millimeters.

An optically transparent means such as a lens or window 82 is positioned within the cavity 54 of bulbous device 20A so as to block the distal-end of the cavity 54 against the inflow of body fluids and tissue components. The window 82 can be made of quartz, sapphire or other optically transparent material. The aperture 79 in the tapered portion 60 defines a communication port between the window 82 and the surrounding exterior of device 20A. The window 82 prevents bodily fluids or materials that have entered the aperture 79 from contaminating the end of optical fiber 14.

Light energy which is emitted from the distal end 18 of fiber 14 impinges upon a surface 84 of lens 82. Radiant energy transmitted through the conduit 14 heats the device 20A when it impinges upon the surface 84. A portion of the radiant energy, however, such as the light beam schematically illustrated as 86 passes through the window 82 and through the aperture 79 directly into the interstitial portion 78 of tubal ostia 34.

The bulbous element 20 is preferably made of metal such as surgical stainless steel, but could also be made of a combination of thermally conductive and thermally insulating materials such as metals and/or ceramics. The exterior surface of the bulbous element 20 is preferably coated with a non-stick or release surface such as poly (tetrafluoroethylene) to provide easy release from the tissue. Poly(tetrafluoroethylene) usually is used for operating temperatures below about 300° C.

The device 20 is preferably constructed and internally dimensioned so that the majority portion of the light energy transmitted down conduit 14 exits through aperture 79 as the light beam 86, with a minority portion of the light energy being converted by the device 20 to heat to raise the temperature of the device 20. This is determined by controlling the diameter of aperture 79.

Referring again to FIG. 1, a laser light source 88 is connected to the proximal end 16 of light transmitting conduit 14. There are several laser sources which could be used. First, the preferred laser source is a Neodymium Yittrium Aluminum Garnet (Nd:YAG) laser having a characteristic wave length of 1064 nanometers. The laser light source 88 preferably is an Nd:YAG laser light source such as for example a Trimedyne 1000 OptiLase™ as marketed by Trimedyne, Inc., of Santa Ana, Calif. Also, a. KTP 532 laser which is an Nd:YAG laser modified to double the frequency and thus provide a characteristic wave length of 532 nanometers may be used. A third choice is an argon gas laser having a characteristic wave length of either 488 or 512 nanometers.

The laser 88 produces the light which is converted by the heat generating element 20 into heat. The word light is used in its broad sense, meaning electromagnetic radiation which propagates through space and includes not only visible light, but also infrared, ultraviolet and microwave radiation.

A beam splitter 90 may be placed in laser transmitting conduit 14 with a further light transmitting conduit 92 connecting the same to a pyrometer 94 in order to monitor the temperature of the device 20.

Sterilization Procedures

The preferred procedures of sterilizing a human female patient will now be described primarily with reference to FIGS. 1 and 4. FIG. 4 is an enlarged view of the area surrounding the left tubal ostia 34 of FIG. 1 showing the heat generating device 20A in place adjacent thereto.

The methods of sterilizing a female patient generally include a first step of inserting into the patient's uterus 12 an elongated energy transmitting conduit 14 having the heat generating device 20 on the distal end 18 thereof.

The heat generating device 20 is maintained in fixed contact with an inner wall 66 of the patient's uterus 12 adjacent the tubal ostia 3,4 for a sufficient time and while transmitting sufficient energy to the heat generating device 20 to coagulate a substantial part of the interstitial portion 78 of the patient's fallopian tube 45 so that the fallopian tube 45 is closed. Subsequently, the procedure is repeated for the patient's second fallopian tube 47.

The procedures of the present invention differ in several significant aspects from the use of somewhat similar apparatus in connection with endometrial ablation procedures.

First, in the present procedure the heat generating device is maintained in fixed contact with the tissue adjacent the tubal ostia for a substantial time, whereas in endometrial ablation procedures there is no significant fixed contact with any portion of the tissue, but rather there is a continuous movement of the laser fiber and/or heated tip across the tissue or a short distance away from the tissue so as to cover very large areas of tissue. The present procedure relies on a fixed contact of the heat generating device with the tissue adjacent the tubal ostia for a substantial time, preferably at least ten seconds while transmitting energy through the conduit 14 to the heat generating device 24. During this time, the heat generating device 20 is heated to a relatively high temperature whereby heat is transmitted to the tissue through direct contact, and additionally that portion of the light energy transmitted out the aperture 79 passes into the interstitial portion of the fallopian tube to aid in coagulating the same. Thus there is a combination of heat conduction from the device 20 into the tissue, and radiant light energy passing through the aperture 79 and falling directly upon the tissue defining the inner surface of the interstitial portion 78 of the fallopian tube 45. As previously mentioned, it is preferred that a majority of the light energy passed through the aperture 79 as radiant energy.

Endometrial ablation also uses much higher power settings than used in the present sterilization procedure. Typical endometrial ablations procedures use a sixty-watt power setting wherein the present procedure preferably only uses about fifteen watts. Fifteen watts would not be enough to accomplish the endometrial ablation because it would not affect the tissue deep enough with the relatively short duration of exposure of the laser to any one area of the tissue in an endometrial ablation procedure.

The geometry of the two preferred tip designs 20A and 20B shown in FIGS. 2 and 3 is very important in the proper placement of the device 20 adjacent the tubal ostia 34. The tapered forward portion 60 of the device 20 is inserted through the tubal ostia 34 thereby centering the heat generating device 20 about the tubal ostia 34 against the inner wall 66 of the uterine cavity 28. Thus the aperture 79 is also centered within the interstitial portion 78 of the fallopian tube so as to direct the radiant laser light energy directly into the fallopian tube.

Utilizing the preferred Nd:YAG laser light source 88, it has been determined that the device 20 is preferably maintained in fixed contact with a patient's uterus adjacent the tubal ostia 34 as shown in FIG. 4 for a time in the range of from about ten to about forty-five seconds while simultaneously transmitting laser energy from the source 88 through the conduit 14 at a rate in the range of about ten to about twenty-five watts. More preferably, the device 20.is maintained in fixed contact with the uterus for a time in the range of from about fifteen to about thirty seconds while simultaneously transmitting laser energy at a rate in the range of from about fifteen to about eighteen watts. It appears that an optimum setting is about fifteen watts for about thirty seconds.

The amount of energy transmitted to the device 20 is chosen so as to result in the heating of the tissue making up the interstitial portion 78 of the fallopian tube 45 to a temperature above about 70° C. so that protein in the tissue is coagulated and less than about 100° C. so as to prevent vaporizing of the tissue. It will be appreciated that too high a temperature, which vaporizes the tissue, would destroy the tissue creating a hole, which is of course undesirable. The desired result is to coagulate the tissue so that the interstitial portion 78 of the fallopian tube will be closed by altered scar type tissue.

EXAMPLE 1

The first clinical trial of sterilization procedures utilizing laser energy was conducted utilizing the prior art device illustrated in FIG. 5 which differs somewhat from the preferred devices of FIGS. 2 and 3 which I have subsequently developed. The device of FIG. 5 includes the light transmitting conduit 14, having a heat generating device 92 attached to the distal end thereof. The device 92 is generally cylindrical in shape and an entire length 94 thereof has a diameter of no greater than about one millimeter. The device 92 may be constructed for example as shown in FIG. 2 of U.S. Pat. No. 4,773,413, or may be any other commercially available heat generating tip having the generally cylindrical geometry just described. Four patients were treated. All patients underwent laparoscopic tubal sterilization in the standard fashion with bipolar electrocautery at the distal portion of the fallopian tube. With simultaneous observation through the laparoscope, a hysteroscope was introduced into the uterine cavity and a one millimeter temperature controlled probe, such as probe 92, was placed through the hysteroscope and guided into the ostia of the fallopian tube as schematically illustrated in FIG. 6. An HGM Argon Model 20S laser source was used. Temperature settings were varied from 150° C. to 400° C. with five-second pulses varying in number from two to fifty. Heat was applied to the tissue at a plurality of locations, as indicated in phantom lines in FIG. 6 as 92A, 92B and subsequently 92C, along the fallopian tubes, a first one of the locations 92A being located the greatest distance into the tube, and subsequent locations 92B and 92C being successively closer to the patient's uterine cavity. Three months following treatment a hysterosalpingogram demonstrated three oviducts were blocked at the corneal portion of the uterus as was anticipated, five others were open to the distal segment of the bipolar electrocautery area. After reviewing the data, it would appear that those successful procedures in which the cornea was blocked were associated with the multiple pulses and higher temperature settings on the laser. It appears from these results that with proper timing and temperature settings the procedure just described could reliably sterilize the patient. I determined, however, that the procedure illustrated in FIG. 6 was not the. preferred procedure, because of difficulties for the physician in manipulating the instrumentation involved. A further significant observation from this data, is that it appears unlikely that prior art endometrial ablation procedures such as those reported by Goldrath and Daniell et al. as discussed above, actually resulted in closing of the fallopian tubes; instead, it appears most likely that the sterilization observed in patients subjected to an endometrial ablation procedure is a result of the destruction of the endometrium rather than the closing of the fallopian tubes. Once the endometrium is destroyed, the patient will be rendered sterile even though the fallopian tubes are still open, because there is no place for a fertilized egg to attach itself to the uterine lining. Since even the least intensive of the trials I conducted would result in more intense localized heating than would the endometrial ablation procedures, it appears unlikely that endometrial ablation procedures consistently result in closing of the fallopian tubes.

EXAMPLE 2

Subsequent to the work described in Example 1, I determined that a much easier procedure for the physician would be one in which it was not necessary to actually insert the heated device into the fallopian tube, but rather to merely place it adjacent the fallopian tube. A subsequent set of clinical tests was performed on three patients utilizing a heated device like that illustrated in FIG. 10 of U.S. Pat. No. 4,773,413 to Hussein et al., marketed by LaserControl Medical Systems Division of Trimedyne, Inc., under the designation Spectraprobe™-80. The Spectraprobe™-80 device is designed so that eighty percent of the laser energy transmitted thereto exits through the forward aperture thereof with the remainder being converted to heat raising the temperature of the device.

The Spectraprobe™-80 device, as illustrated in FIG. 10 of U.S. Pat. No. 4,773,413 does not have a tapered forward tip, but instead has a rounded forward bulbous surface. The Spectraprobe™-80 was utilized on three patients utilizing a Cooper Model 8000 Nd:YAG laser. The tests were run at a variety of time and power settings to observe the effect of utilizing various amounts of energy, as set forth in the following descriptions.

Patient A

This patient was placed in a semi-lithotomy position, prepped with Betadine Scrub and draped in sterile linens in the usual manner for a laparoscopic procedure. 1 cm incision made below the umbilicus. Veress needle instilled approximately 3 liters. Pelvic cavity was visualized. The fallopian tube on the left was identified and fulgurated near the fimbriated end of the fallopian tube. The right tube was adherent up under some omentum and other adhesions. Therefore, it was fulgurated approximately 2 cm from the cornua. Following this, the laparoscope was left in place and the hysteroscope was placed after dilating the cervix to a size 20 Heaney dilator. 8 mm hysteroscope was placed. A Spectraprobe™-80 tip was placed through the hysteroscope and placed adjacent to the left cornual ostia and was fired at fifteen watts for thirty seconds. Blanching was noted on the fundal side of the surface and the Spectraprobe™-80 tip was noted to be near the surface of the fundus. Some fluid exuded through the thin portion of the fundus at that point. No further bleeding was encountered. The laser probe was removed and a 1 mm heat probe was inserted and attached to a Model 20 S Argon laser and was placed in the os on the right side and fired at 400 degrees for five seconds on three occasions. The procedure was terminated. The laparoscopic incision was re-examined. No abnormal bleeding appeared to be present. The one area on the sigmoid colon had a bloody patch to it, did not appear to have any blanching consistent with any type of laser energy impact. The surface was washed copiously with saline and appeared to have a superficial wound. No active bleeding was encountered. Also, adhesions were noted on initial entry of the laparoscope and these adhesions were fulgurated with bipolar cautery and cut with sharp scissors. That was to visualize the pelvis on initial entry of the laparoscope. $CO_2$ was allowed to escape. Incisions were closed with subcuticular suture of 4-0 Vicryl and the patient was taken to the recovery room in good condition. Estimated blood loss less than 5 cc. Note that this first patient had the procedure like that of FIG. 6 on the right side as a comparison to the newer procedure which was used on the left side. Three months later a hysterosalpingogram showed both ostia to be closed.

Patient B

The patient was placed in a semi-lithotomy position and pepped with Betadine scrub and draped with sterile linens in the usual manner for laparoscopic procedure. A 1 cm incision was made below the umbilicus and Verres needle was instilled approximately 3 liters. The 10 mm trocar was introduced through the same incision. The pelvic cavity was visualized and the 6 mm trocar was introduced through the lower midline incision. The. bowel was pushed up out of the pelvis with a blunt probe. The uterus was noted to be retroflexed and slightly enlarged. The fallopian tubes were identified, fulgurated at their distal end on either side with bipolar electrocautery without difficulty. Following this the uterus was sounded to 8 cm and noted to be retroflexed and somewhat irregular, dilated to size #18 Heaney dilator. The intrauterine cavity was visualized. The right ostia was identified and the Spectraprobe™-80 tip was placed in the osteal opening and the laser was turned on at fifteen watts for thirty seconds. The opposite ostia was then identified on the left side and the Spectraprobe™-80 tip was placed in the os and fired for fifteen watts for fifteen seconds. The patient tolerated the procedure well and no unusual bleeding was encountered. Instruments were removed. The $CO_2$ was allowed to escape. The incisions were closed with subcuticular sutures of 4-0 Vicryl. Three months later, a hysterosalpingogram showed both ostia to be closed.

Patient C

The patient was placed in the lithotomy position, prepped with Betadine scrub and draped with sterile linens for laparoscopic procedure. A 1 cm incision was made below the umbilicus. A Verres needle instilled approximately three liters. A 10 mm trocar was introduced through the same incision. The pelvic area was visualized and the 6 mm trocar was introduced through a lower midline incision. The fallopian tubes were identified and fulgurated at the distal portion with bipolar electrocautery on either side without difficulty. Following this, the laparoscope was left intact and the hysteroscope was placed through the cervix after dilating it to a size #18 Heaney dilator. It was somewhat difficult to visualize the ostia in this patient, on the left side particularly. The right side was more easily seen. A, Spectraprobe™-80 tip was placed at the ostial opening and fired for thirty seconds at eighteen watts. This was carried in the same exact fashion on the opposite side while under direct vision through the laparoscope. By second person, blanching was noted to appear at the cornual portions on both sides without difficulty. There were no further abnormalities noted. The instruments were removed and the incisions abdominally were closed with a subcuticular stitch of 4-0 Vicryl. Three months later a hysterosalpingogram showed the left ostia (which had been difficult to locate) to be open, and showed the right ostia to be closed.

On Patients A and B, Lupron Depot 3.75 milligrams was given preoperatively on the third day of the menstral cycle. Lupron is a gonadatropin releasing hormore agonist which stops all hormone production of the ovaries and therefore stops estrogen production. This stops stimulation of the endometrium which makes the tissue thinner and allows better visualization of the ostia.

In summary re Example 2, of the five tubal ostia treated with the Spectraprobe™-80 tip, four were closed by the procedure. The one which was not (left side on Patient C) had been difficult to locate. Also, Patient C had not received the Lupron preoperatively. Several conclusions can be made from these results. First, the procedure utilizing a heated tip placed against the tubal ostia with a portion of the laser energy directed through an aperture into the fallopian tube appears to be successful; four out of five tests were successful, with the failure of the fifth being explained by difficulty in locating the tubal ostia. Second, the difficulty encountered in locating the left tubal ostia of Patient C and placing the heated device adjacent thereto illustrates the desirability of a tip having a tapered forward portion such as illustrated in FIGS. 2 and 3 to aid in accurately placing the device centered against the tubal ostia. Third, the desirability of the preoperative Lupron medication is illustrated to aid in the subsequent visualization of the tubal ostia.

It is believed that the procedures set forth herein provide many advantages as compared to present day sterilization procedures. Most significantly these procedures are capable of being administered on an out-patient basis with no need for general anesthetic.

Thus it is seen that the apparatus and methods of the present invention readily achieve the ends and advantages mentioned as well as those inherent therein. While certain preferred embodiments of the invention have been illustrated and described for purposes of the present disclosure, numerous changes may be made by those skilled in the art which changes are encompassed within the scope and spirit of the present invention as defined by the appended claims.

What is claimed is:

1. A method of sterilizing a female patient, comprising:
   (a) inserting into the patient's uterus an elongated light transmitting conduit having a distal end;
   (b) transmitting light energy through said conduit and thereby providing heat;
   (c) applying said heat to a portion of the patient's uterus adjacent one of the patient's tubal ostia, thereby coagulating a substantial part of tissue defining an inner surface of the interstitial portion of the patient's fallopian tube associated with said one of the patient's tubal ostia so that the fallopian tube is closed; and
   (d) repeating step (c) for the other of the patient's fallopian tubes, so that both fallopian tubes are closed and the patient is sterilized.

2. The method of claim 1 wherein said portion of said patient's uterus is an inner wall of said uterus.

3. The method of claim 1 wherein at least a portion of the light energy transmitted through said conduit passes through said distal end into said fallopian tube to aid in coagulating said interstitial portion of said fallopian tube.

4. The method of claim 3 wherein said portion of said light energy passed through said distal end is a majority portion of the light energy transmitted through said conduit.

5. The method of claim 1 wherein step (c) further comprises maintaining said heat on said portion of said patient's uterus for at least ten seconds.

6. The method of claim 1 wherein:
   in step (a), said light transmitting conduit has a Neodymium-YAG laser light source operatively connected to a proximal end of said conduit;
   step (b) comprises transmitting laser energy from said source through said conduit at a rate in the range of about ten to about twenty-five watts; and
   step (c) further comprises maintaining said heat on said portion of said patient's uterus for a time in the range of about ten to about forty-five seconds so that tissue making up the interstitial portion of the fallopian tube is heated to a temperature above 70° C. so that protein in the tissue is coagulated in less than about 100° C. so as to prevent vaporizing of the tissue.

7. The method of claim 6 wherein:
   step (b) further comprises transmitting laser energy from said source through said conduit at a rate in the range of about fifteen to about eighteen watts; and
   step (c) further comprises maintaining said heat on said portion of said patient's uterus for a time in the range of about fifteen to about thirty seconds.

8. A method of sterilizing a female patient, comprising:
   (a) inserting into the patient's uterus an elongated light energy transmitting conduit having a distal end;
   (b) transmitting light energy through said conduit such that at least a portion of the transmitted energy generates heat; and
   (c) coagulating tissue adjacent to the patient's fallopian tubes and thereby closing the patient's fallopian tubes by applying said heat to said tissue.

9. The method of claim 8 wherein step (c) further comprises applying said heat to said tissue at a plurality of locations along the fallopian tubes, a first one of said locations being located the greatest distance into said tubes, and subsequent positions being successively closer to the patient's uterine cavity.

10. The method of claim 8 wherein step (c) is further characterized by placing said distal end of said conduit adjacent each of the patient's tubal ostia.

11. A method of sterilizing a female patient, comprising:
   (a) inserting into the patient's uterus an elongated light transmitting conduit having a distal end;
   (b) positioning said distal end of said conduit adjacent one of the patient's tubal ostia;
   (c) transmitting light energy through said conduit and converting at least a portion of said energy to heat causing said fallopian tube to be closed due to alteration of tissue adjacent thereto; and
   (d) repeating steps (b) and (c) for the patient's other tubal ostia and associated other fallopian tube.

12. The method of claim 11 wherein:
   in step (a), said light transmitting conduit has a Neodymium-YAG laser light source operatively connected to a proximal end of said conduit; and
   step (c) further comprises maintaining said heat on said tissue for a time in the range of from about ten to about forty-five seconds while simultaneously transmitting laser energy from said source through said conduit at a rate in the range of about ten to about twenty-five watts.

13. The method of claim 12 further comprising heating tissue making up an interstitial portion of said fallopian tubes to a temperature above about 70° C. so the protein in the tissue is coagulated in less than about 100° C. so as to prevent vaporizing of the tissue.

14. The method of claim 13 wherein step (c) further comprises maintaining said heat on said tissue for a time in the range of about fifteen to about thirty seconds while simultaneously transmitting laser energy from said source through said conduit at a rate in the range of about fifteen to about eighteen watts.

15. The method of claim 11 wherein step (c) comprises heating tissue making up an interstitial portion of said fallopian tubes to a temperature in the range above about 70° C. so the protein in the tissue is coagulated and less than about 100° C. so as to prevent vaporizing of the tissue.

16. The method of claim 11 wherein step (c) further comprises maintaining said heat on said tissue for a time in the range of about fifteen to about thirty seconds while substantially transmitting laser energy from a laser light source through said conduit at a rate in the range of about fifteen to about eighteen watts.

* * * * *